US007070789B2

United States Patent
Mebatsion et al.

(10) Patent No.: US 7,070,789 B2
(45) Date of Patent: Jul. 4, 2006

(54) RECOMBINANT NEWCASTLE DISEASE VIRUS NUCLEOPROTEIN MUTANT AS A MARKER VACCINE

(75) Inventors: Teshome Mebatsion, RJ Boxmeer (NL); Marcus Josephus Marie Koolen, BZ Houten (NL)

(73) Assignee: Akzo Nobel N.V., Arnhem (NL)

( * ) Notice: Subject to any disclaimer, the term of this patent is extended or adjusted under 35 U.S.C. 154(b) by 234 days.

(21) Appl. No.: 10/415,981

(22) PCT Filed: Oct. 30, 2001

(86) PCT No.: PCT/EP01/12573

§ 371 (c)(1),
(2), (4) Date: May 2, 2003

(87) PCT Pub. No.: WO02/36617

PCT Pub. Date: May 10, 2002

(65) Prior Publication Data

US 2004/0043035 A1    Mar. 4, 2004

(30) Foreign Application Priority Data

Nov. 2, 2000    (NL)    .................................. 00203814

(51) Int. Cl.
*A61K 39/17*    (2006.01)
(52) U.S. Cl. .............................. 424/214.1; 424/192.1; 435/6
(58) Field of Classification Search ............. 424/199.1, 424/214.1, 192.1; 435/6, 320.1; 530/300
See application file for complete search history.

(56) References Cited

U.S. PATENT DOCUMENTS 6,146,642 A * 11/2000 Garcia-Sastre et al. .. 424/214.1

FOREIGN PATENT DOCUMENTS

EP    0 974 660    1/2000

OTHER PUBLICATIONS

A. Romer-Oberdorfer et al: "Generation of recombinant lentogenic Newcastle disease virus from cDNA"; J. Gen. Virol., vol. 80, 1999, pp. 2987-2995.
S. Rautenschlein et al: "Embryo vaccination of turkeys against Newcastle disease infection with recomvinant fowlpox virus constructs containing interferons as adjuvants"; Vaccine, vol. 18, 2000 pp. 426-433; table 2-4.
A. Makkay et al: "Antibody detection based differential ELISA for NDV infected or vaccinated chickens versus NDV Hn subunit vaccinated chickens"; Veterinary Microbiology, vol. 66, 1999, pp. 209-222.
M. Ward et al: "Nucleotide sequence and vaccinia expression of the nucleoprotein of a highly virulaent nurtopic strain of Newcastle disease virus" Avian Diseases, vol. 44, 2000 pp. 34-44.

* cited by examiner

*Primary Examiner*—Ali R. Salimi
(74) *Attorney, Agent, or Firm*—William P. Ramey; William M. Blackstone

(57) ABSTRACT

The present invention provides a NDV mutant that is suited as a marker vaccine strain. The NDV mutant is not able to express an immunodominant epitope of the nucleoprotein (NP).

20 Claims, 11 Drawing Sheets

Figure 2

Figure 1:
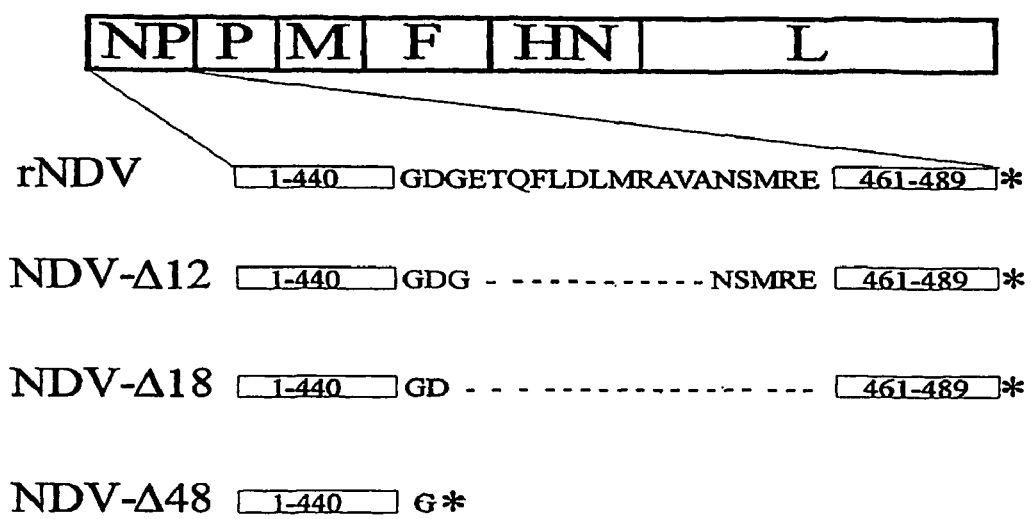

Serological response of SPF chickens immunized with NDV-Δ18, inactivated or live ND vaccines Figure 3  Attenuation of NDV-Δ18

Figure 4    NDV-Δ18 in ovo either alone or combined with another vector vaccine

Figure 5 Measurement of chicken sera in HI

NDV-MHV1, NDV HI titers

Figure 6  Measurement of chicken sera in NDV whole-virus ELISA

NDV-MHV1, NDV ELISA titers

Figure 7  Measurement of chicken sera in HI

NDV-MHV2, NDV HI titers

Figure 8   Measurement of chicken sera in NDV whole-virus ELISA

NDV-MHV2, NDV ELISA titers

Figure 9  Measurement of chicken sera in MHV ELISA

NDV-MHV1, serum dilution: 1/225

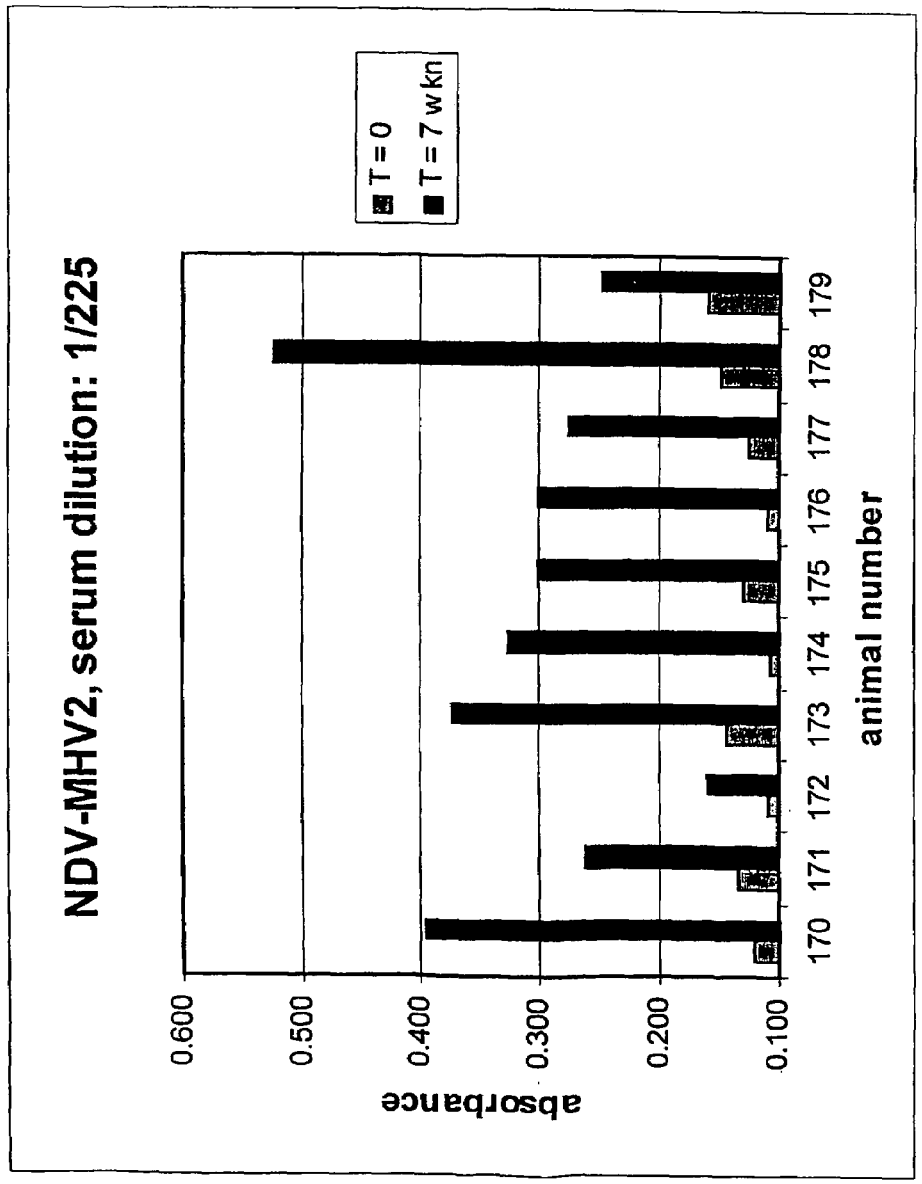
Figure 10  Measurement of chicken sera in MHV ELISA

Figure 11  Measurement of chicken sera in MHV ELISA

NDV-d18, serum dilution: 1/225

RECOMBINANT NEWCASTLE DISEASE VIRUS NUCLEOPROTEIN MUTANT AS A MARKER VACCINE

Newcastle disease virus (NDV) is responsible for one of the most devastating diseases of poultry and has substantial economic impact in the poultry industry. Vaccination of chickens, particularly those raised for commercial consumption, is carried out throughout the world. Although effective live or inactivated ND vaccines are currently available, the virus remains an ongoing threat to commercial flocks.

The negative-strand RNA virus genome of NDV, which is about 15 kb in length, contains six genes encoding six major structural proteins: nucleoprotein (NP), phosphoprotein (P), matrix protein (M), fusion protein (F), haemagglutinin-neuraminidase (HN) and RNA-dependent RNA polymerase (L). The RNA together with NP, P and L protein forms the ribonucleoprotein complex (RNP) that serves as a template for RNA synthesis. A common feature of all negative-strand viruses (NSV) is the presence of their genetic information exclusively in a form of a RNP. The RNP, but not the naked RNA, serves as a template for transcription and replication.

The NP together with the polymerase proteins, P and L, plays an eminent role in encapsidating and protecting the RNA from enzymatic degradation. Moreover, NP regulates transcription and replication of the viral genome by interacting with P alone, with P and L (RNA polymerase) or with it self (NP-NP interaction). For Sendai paramyxovirus, it was shown that a conserved N-terminal region of NP was involved in NP-RNA and NP-NP interaction (Buchholz et al., J. Virol. 67, 5803–5812, 1993), whereas the carboxy-terminal domain was shown to be required for template function (Curran et al., J. Virol. 67, 4358–64). Most parts of the NP are thus absolutely essential for virus replication due to multifold engagement of NP in the assembly and biologic activity of the RNP.

In many countries, legislation to control NDV outbreaks already exists. In some countries, eradication policies with compulsory elimination of infected birds are practiced. For continuation of successful international poultry trades, introduction of systematic ND control measures is desirable. However, all currently used whole virus based live and inactivated ND vaccines have a major drawback, in that vaccinated animals cannot be distinguished from infected animals with standard serological tests like haemagglutination inhibition (HI) or virus neutralization (VN). Therefore, there is a need for NDV immunogenic material comprising a NDV protein lacking at least one immunodominant epitope. An epitope is a small structural region on an antigen that interacts with an antibody. An epitope may consist of little as three amino acids of a polypeptide, but usually comprises 5–10 or in some instances more amino acids.

Recently, vaccines termed, "marker vaccines" are gaining popularity in veterinary medicine where eradication of specific diseases is of national or international interest. A marker vaccine is defined as a vaccine, in conjunction with a diagnostic test, that enables serological differentiation of vaccinated animals from infected animals.

Approaches to develop marker vaccines include deletion of one or more nonessential, but immunogenic genes. This approach is mainly applicable for DNA viruses containing several dispensable genes (e.g. herpes viruses). For RNA viruses, most of the genes are either essential or the nonessential ones are not immunogenic. NDV, a negative strand RNA virus, contains six major structural genes, which are all essential for propagation of the virus. Deletion of one or more genes would be expected to cause loss of biological activities. Indeed, whereas such control programs for other viral infectious diseases in animals are under development, until the present invention a vaccine based on a NDV vaccine strain which would fit in ND control programs has not been described yet.

An alternative approach for the development of a marker vaccine is the use of "subunit vaccines". This approach has been implemented for NDV by identifying two glycoproteins, fusion protein (F) and haemagglutinin-neuraminidase (HN), involved in inducing protective immunity. Recombinant vectors, such as herpesvirus of turkey (HVT) and fowlpox virus (FPV) expressing NDV F and/or HN have been successfully constructed and their safety and efficacy have been extensively studied.

Nucleoproteins (NP) of negative-strand RNA viruses (NSV) are highly immunogenic in nature and have been used as an antigen in diagnostic ELISAs. These include rabies, measles, rinderpest, vesicular stomatitis virus and NDV. These tests were mainly used to monitor vaccination programs. In conjunction with a NDV HN-subunit vaccine, a NP based immunoassay was also described as a diagnostic test in differentiating between vaccinated and infected animals (Makkay et al., Vet. Microbiol. 66, 209–222, 1999). However, NP immunoassays in conjunction with a whole NSV based marker vaccine, in particular NDV vaccine, does not exist, mainly due to the fact that genetic modification of the very vital NP gene is expected to have detrimental consequences on virus replication and infectivity.

A drawback of the NDV subunit vaccines is, however, that the efficacy of recombinant viruses expressing NDV F or HN protein is reduced significantly in the presence of maternal derived antibodies (MDA) in commercial chickens. In contrast, conventional ND vaccines based on whole virus preparation confer full protection even in the presence of MDA.

Another general draw back of several of the recombinant vectors is the delayed onset of protective immunity. Conventional live ND vaccines generally give full-protection 6–7 days after vaccination whereas the onset of immunity induced by a vaccine based on a recombinant HVT expressing NDV F protein was shown to occur between 14 and 21 days post-vaccination (Morgan et al., Avian Dis. 37, 1032–1040, 1993).

In view of these drawbacks of ND subunit vaccines there is a need for a ND marker vaccine based on whole virus that retains its F- and HN protein in their native form and that can be serologically discriminated from wild type- as well as traditional vaccine viruses.

International application WO 99/66045 discloses a NDV marker vaccine based on a genetically modified NDV mutant lacking an immunodominant epitope on a NDV protein. However, this vaccine virus contains a hybrid HN protein composed of only one-fourth part of the HN protein from NDV while the remaining part of the HN protein is derived from an unrelated avian paramyxovirus type 2 or 4. The removal of the majority of the NDV HN region would conceivable reduce the role played by HN in inducing NDV protective antibody.

Currently available live NDV vaccines can only be administered to hatched chickens through drinking water, aerosol, eye drops or by parenteral routes. These methods of applications have some disadvantages. Most importantly, these methods are expensive because of the labour needed for their application. Recently, the use of vaccines as embryo vaccines has proved to be effective and economical (Sharma and Burmester, Avian Diseases 26, 134–149, 1982 and Sharma, Avian Diseases 29, 1155–1169, 1985). Moreover, embryo vaccination was found to be advantageous due to early age of resistance to the specific disease and administration of a uniform dose of vaccine into each egg using semiautomatic machines with multiple injection heads.

It should be noted that many vaccines used conventionally for post-hatch vaccination of birds could not be used for in ovo vaccination. Late stage embryos are highly susceptible to infection with most vaccine viruses examined, including those vaccine viruses which can safely be used in one-day-old hatched chicks. Consequently, conventional vaccines cannot be used for in ovo administration.

Presently, there is no suitable commercially available ND vaccine that can be applied in ovo, mainly due to high level of embryo mortality associated even with two of the mildest commercially available NDV vaccine strains: NDW (U.S. Pat. No. 5,149,530) and C2 (U.S. Pat. No. 5,750,111).

U.S. Pat. No. 5,427,791 (Regents of the University of Minnesota) discloses the use of chemical mutagenic agents to produce NDV mutants of the Hitchner B1 strain that are non-pathogenic for late stage embryos. Chemical treatment of the B1 strain with ethyl methanine sulfonate (EMS) resulted in the mutant virus NDV-B1-EMS, which could be safely administered to chicken eggs at embryonation day of 18. However, disadvantageously, each egg passage step of this strain must be carried out in the presence of the mutagenic agent EMS because of the property of the mutant to revert back to the parent B1 strain which is not safe for embryos.

It is an object of this invention to provide a NDV mutant that can be used as the active component in a whole virus based ND marker vaccine to allow serological distinction between animals infected with wild-type NDV or vaccinated with conventional NDV vaccine strains from that of animals immunised with a vaccine based on this NDV mutant.

It is a further object of the present invention to provide a NDV mutant that can be used as the active component in a vaccine that can be administered not only to young birds after hatch, but which can also be administered safely in ovo.

The invention described here meets these objects by providing a genetically engineered NDV mutant that is distinct from known NDV (vaccine) strains due to the removal of a novel immunodominant epitope from the NP, which is serologically very relevant in NDV infection, but the deletion of which does not adversely affect the protective properties of the new NDV mutant.

The present invention provides a NDV mutant lacking an immunodominant epitope on a NDV protein as a result of a mutation in a gene encoding the protein, characterised in that the NDV mutant lacks an epitope located within a region of the nucleoprotein (NP), the region having the amino acid sequence (447–455) shown in SEQ ID No. 1.

It has been found that the amino acid sequence (447–455) Phe Leu Asp Leu Met Arg Ala Val Ala of the NP, encoded by nucleotides 1460–1486 of the NDV genome, comprises an immunodominant epitope of the NDV NP. That is to say that antisera obtained from virtually all chickens infected with NDV interacts with an epitope located in this region. The antisera do interact with the amino acids mentioned above, but do not substantially interact with amino acids flanking this region.

Furthermore, it is demonstrated in FIG. 2 that chicken antiserum induced by both live and inactivated, conventional NDV strains react with the NP 18-mer peptide spanning amino acids (443–460) Gly Glu Thr Gln Phe Leu Asp Leu Met Arg Ala Val Ala Asn Ser Met Arg Glu (SEQ ID No. 2) comprising the (447–455) region. A comparison of the amino acid sequences encompassing this region reveals 100% amino acid identity among the velogenic Texas GB strain, the mesogenic Beaudette C strain and the lentogenic Clone-30 strain. Therefore, one of the important criteria for developing a marker vaccine, i.e. the identification of an epitope expressed by a protein of conventional NDV strains that is recognised by the chicken immune system, is fulfilled.

The numbering in brackets as used herein to identify nucleotide positions on the NDV genome and amino acid residues in the NDV proteins is as described by Römer-Oberdörfer et al., J. Gen. Virol. 80, 2987–2995, 1999, EMBL accession no. Y18898).

Unexpectedly, it has been further found that despite the fact that the NP is an essential protein for NDV replication, the amino acids (447–455) are not required for virus replication. An infectious recombinant NDV mutant that does not express a NP epitope located within this region was successfully recovered from cells after transfection of these cells with the appropriate plasmids using the "reverse genetic" technology, and could be propagated efficiently in chicken eggs.

A NDV NP mutant according to the present invention was generated by introducing a mutation in the NP gene such that the ability of the immunodominant epitope to induce antibodies in chickens that are reactive with an epitope located within the 18-mer peptide having the amino acid sequence (443–460) was lost. Examples 2 and 3 demonstrate (i) that the NDV NP mutant according to the invention is able to induce HI antibodies and polyclonal chicken anti-NDV sera that react with whole virus antigen, but that (ii) these antisera show no reactivity with an epitope located within the 18-mer peptide.

The observation that chicken anti-NDV sera raised against the NDV NP mutant according to the present invention can be distinguished from chicken sera raised against naturally occurring NDV strains and conventional NDV vaccine strains by examining the interaction of the antisera with an epitope located within the (447–455) region makes this NDV NP mutant a suitable candidate for a marker vaccine. In particular, the present invention also includes a NDV NP mutant lacking an immunodominant epitope located within the (447–455) region that induces antiserum in chickens that can be distinguished from antiserum induced by conventional NDV strains by examining the interaction of the mutant antiserum with a peptide comprising the (447–455) region in the presence of a monoclonal antibody that specifically binds with an immunodominant epitope located in this region. In the latter case, the examination is usually an immunological competition- or blocking assay.

Therefore, a particular NDV NP mutant according to the present invention is characterised in that the mutant induces antiserum in chickens lacking antibodies that react with an immunodominant epitope located within the amino acid region (447–455) of the NP.

In a more preferred embodiment a NDV NP mutant is provided that induces antiserum in chickens that lacks antibodies that react with an 18-mer peptide having the NP amino acid sequence (443–460) shown in SEQ ID No. 2.

With the term "induces antiserum in chickens lacking antibodies that react with" is meant that a serum sample obtained from an infected/vaccinated chicken is scored negative in a direct- or blocking NP enzyme-linked immunosorbant assay (ELISA).

Typically, the absorbance (OD) cutt-off value for the NP ELISA to differentiate positive from negative samples is set at three standard deviations above the average P/N ratios of negative control samples from SPF chickens (where P=the OD of samples from wells coated with a relevant peptide coupled to a carrier molecule and; N=the OD of samples from wells coated with the carrier molecule). A carrier molecule can be a carrier protein, such as BSA, ovalbumin, KLH, a carbohydrate chain or a synthetic amino acid chain.

The NP gene is located on the NDV genome at nucleotide positions 56 to 1801 (NDV strain Clone 30®). The NP of NDV is 489 amino acids long and is highly conserved within lentogenic, mesogenic and velogenic strains. The nucleotide sequence and the amino acid sequence of the NP gene of this NDV strain are shown in SEQ ID no. 3 and 4. A comparison of the deduced amino acid sequences of the NP of Clone-30 with the corresponding sequences of the velogenic Texas GB- and the mesogenic Beaudette C strains of NDV reveals 100% and 99.3% identity. In case a polypeptide region is defined herein by reference to a specific amino acid sequence derived from the specific NDV strain Clone 30, this region is considered to encompass the corresponding region with a deviating amino acid sequence of another NDV strain.

A mutation is understood to be a change of the genetic information in a "wild-type" or unmodified NP gene of a parent NDV strain which is able to express a native NP such that the NP expressed by the NDV mutant lacks an immunodominant epitope located within the (447–455) region of the NP.

A further requirement of the mutation introduced in the NP gene is that the altered NP allows the recovery of infectious NDV from cell culture after transfection of these cells with the appropriate plasmids using the "reverse genetic" technology for NDV. Examples 1 and 2 describe experiments that are suitable for determining the ability of the altered NP to induce NDV antibodies and the permissibility of the mutation to generate infectious virus recoverable from cell culture transfected with the appropriate plasmids.

The mutation is, for example, a nucleic acid substitution, deletion, insertion, or a combination thereof In a preferred embodiment of the present invention the NDV NP mutant comprises a deletion or substitution of one or more amino acids in a region of the NP having the amino acid sequence (447–455) shown in SEQ ID. No. 1.

It has been found herein that not all deletions in the region of the NP gene comprising the coding sequences of an immunodominant epitope are permissible. A deletion of the nucleotides corresponding to NP amino acids 443–460 (NDV-Δ18 mutant) lead to the recovery of an Infectious NDV mutant from cell culture after transfection with the appropriate plasmids, whereas deletion of the nucleotides corresponding to NP amino acids 444–455 (NDV-Δ12 mutant) or 442–489 (NDV-Δ48 mutant) did not.

Analysis of the protein secondary structure (Garnier-Osguthorpe-Robson analysis) showed that amino acid positions 444–459 of the NP forms an alpha-helix. It is found that removal of the complete helix and flanking nucleotides (Δ443–460) did not prevent the generation of viable, infectious recombinant NDV, whereas removal of the partial helix structure or additional parts of the NP protein did not lead to the recovery of infectious NDV from cell culture.

Therefore, a preferred NDV mutant according to the present invention comprises a deletion of the amino acids 443±1–460±1.

In a particular preferred aspect of this embodiment of the invention a NDV NP mutant is provided that comprises a deletion of the amino acids 443–460.

A particularly advantageous NDV mutant according to the present invention is a NDV mutant as described above which comprises additional attenuating mutations. Such NDV mutants can be derived from any conventional ND vaccine strain. Examples of such suitable NDV vaccine strains present in commercially available ND vaccines are: Clone-30®, La Sota, Hitchner B1, NDW, C2 and AV4, Clone-30® being the preferred vaccine strain.

In a further aspect of this embodiment the present invention provides a recombinant vector virus based on the NDV mutant described above. Such a recombinant vector virus can be used not only for the preparation of a vaccine against NDV, but also against other poultry infectious diseases. Alternatively, such a recombinant vector virus may also provide an extra security in a diagnostic test and makes the recombinant viruses attractive dual marker candidates.

A NDV vector can be obtained by in-frame substitution (complete or partial) of the region encoding the NP immunodominant epitope defined above by a heterologous nucleic acid sequence encoding an immunodominant epitope of a polypeptide other than the NP, e.g. a polypeptide of another avian pathogen. The immunodominant epitope represents a region of a polypeptide that interacts with virtually all antisera induced by (a composition comprising) the polypeptide.

In a preferred NDV vector according to the present invention the nucleotides encoding the NP amino acid sequence 444–459 or 444–455 are substituted by a heterologous nucleotide sequence, in particular by a heterologous nucleotide sequence encoding 16 or 12 amino acids, respectively.

In example 5 it is demonstrated that a B-cell epitope of a virus unrelated to NDV can be used to replace the NP-immunodominant epitope of NDV. The recombinant NDV vectors were able to induce specific antibodies against the foreign epitope without inducing antibodies directed against the immunodominant epitope on the NP. Furthermore, it is demonstrated that the expressed foreign epitope is able to induce protection against challenge by the corresponding wild-type virus.

A NDV vector can also be obtained by inserting a heterologous nucleic acid sequence encoding a polypeptide of another avian pathogen into a non-translated region of the NDV mutant. Non-translated regions suitable for this purpose are located between the genomic promoter and the start of the NP gene, and at the NP/P, P/M, M/F, F/HN and HN/L gene junctions as well as between the end of the L gene and the antigenomic promoter. The heterologous nucleic acid sequence may encode an antigen of an avian pathogen such as infectious bursal disease virus, infectious bronchitis virus, Marek's disease virus, avian encephalomyelitis virus, avian reovirus, avian influenza virus, chicken anaemia virus, Salmonella spp., E. coli, and Eimeria spp.

A NDV NP mutant according to the present invention can be prepared by means of the well established "reverse genetics" method that enables the genetic modification of non-segmented, negative stranded RNA viruses (reviewed by Conzelmann, Annu. Rev. Genet. 32, 123–162, 1998, and Roberts and Rose, Virology 247, 1–6, 1998).

Additionally, such a method has also been disclosed for NDV by Peeters et al. (J. Virology 73, 5001–5009, 1999) and Römer-Oberdörfer et al. (J. Gen. Virol. 80, 2987–2995, 1999) and is described in Example 1.

The desired mutations can be introduced into the NDV genome by means of methods generally known in the art for this purpose. In particular, the mutations are introduced by means of site-directed mutagenesis. Such a method is described herein, but is also generally used in the art (Peeters et al., 1999, supra; Current Protocols in Molecular Biology, eds.: F. M. Ausubel et al., Wiley N.Y., 1995 edition, pages 8.5.1.–8.5.9, and Kunkel et al., Methods in Enzymology Vol.154, 376–382, 1987).

In addition to the unexpected finding that a NDV NP mutant according to the present invention is able to induce an antibody response in chickens that can be distinguished from that induced by naturally occurring NDV strains, it has also been found that the NDV NP mutant described above is able to induce a protective immune response.

Therefore, in another embodiment of this invention a vaccine against Newcastle disease in poultry is provided that comprises a NDV NP mutant as defined above in a live or inactivated form, and a pharmaceutically acceptable carrier or diluent.

A vaccine according to the invention can be prepared by conventional methods such as those commonly used for the commercially available live- and inactivated NDV vaccines.

Briefly, a susceptible substrate is inoculated with the NDV NP mutant and propagated until the virus replicated to a desired titre after which NDV containing material is harvested. Subsequently, the harvested material is formulated into a pharmaceutical preparation with immunising properties.

Every substrate which is able to support the replication of ND viruses can be used in the present invention, including primary (avian) cell cultures, such as chicken embryo fibroblast cells (CEF) or chicken kidney cells (CK), or mammalian cell lines such as the VERO cell line or baby hamster kidney (BHK) cell line.

A particularly suitable substrate on which the NDV NP mutant can be propagated are SPF embryonated eggs. Embryonated eggs can be inoculated with, for example 0.2 ml NDV containing allantoic fluid comprising at least $10^{2.0}$ $EID_{50}$ per egg. Preferably, 9- to 11-day old embryonated eggs are inoculated with about $10^{5.0}$ $EID_{50}$ and subsequently incubated at 37° C. for 2–4 days. After 2–4 days the ND virus product can be harvested preferably by collecting the allantoic fluid. The fluid can be centrifuged thereafter for 10 min. at 2500 g followed by filtering the supernatant through a filter (100 μm).

The vaccine according to the invention comprises the NDV NP mutant together with a pharmaceutically acceptable carrier or diluent customary used for such compositions.

The vaccine containing the live virus can be prepared and marketed in the form of a suspension or in a lyophilised form. Carriers include stabilisers, preservatives and buffers. Diluents include water, aqueous buffer and polyols.

If desired, the live vaccine according to the invention may contain an adjuvant. Examples of suitable compounds and compositions with adjuvant activity are the same as mentioned below for the inactivated NDV vaccine.

Although administration by injection, e.g. intramuscular, subcutaneous of the live vaccine according to the present invention is possible, the vaccine is preferably administered by the inexpensive mass application techniques commonly used for NDV vaccination. For NDV vaccination these techniques include drinking water and spray vaccination.

An additional unexpected property of a NDV NP mutant according to the invention is that its virulence for chicken embryos is significantly attenuated such that it can be administered in ovo. Therefore, the present invention also provides a vaccine based on a NDV NP mutant as described above that can be used for in ovo vaccination.

The vaccine comprising the NDV NP mutant can be injected into embryonated eggs according to conventional in ovo vaccination methods. Usually, the vaccine is injected into embryonated eggs during late stages of the embryonation, generally during the final quarter of the incubation period (day 15–21), preferably at day 18 or 19 of the incubation period. The mechanism of injection of the incubated eggs is not particularly critical provided that it does not unduly damage tissue and organs of the embryo. For example, a small hole is pierced with a needle (1–1½ inch, about 22 gauge) attached to syringe in the large end of the shell and the vaccine is injected below the inner shell membrane and the chorioallantoic membrane. Subsequently, the vaccinated embryonated eggs are transferred to an incubator to hatch (U.S. Pat. Nos. 4,458,630, 5,427,791, WO 98/56413 and WO 95/35121). Preferably, the whole embryo vaccination process is carried out using automated vaccination systems, such as the commercially available Inovoject®.

In another aspect of the present invention a vaccine is provided comprising the NDV NP mutant in an inactivated form. The major advantages of an inactivated vaccine are its safety and the high levels of protective antibodies of long duration that can be induced.

The aim of inactivation of the viruses harvested after the propagation step is to eliminate reproduction of the viruses. In general, this can be achieved by well known chemical or physical means.

A vaccine containing the inactivated NDV NP mutant according to the invention can, for example, comprise one or more of the above-mentioned pharmaceutically acceptable carriers or diluents suited for this purpose.

Preferably, an inactivated vaccine according to the invention comprises one or more compounds with adjuvant activity. Suitable compounds or compositions for this purpose include aluminium hydroxide, -phosphate or -oxide, oil-in-water or water-in-oil emulsion based on, for example a mineral oil, such as Bayol F® or Marcol 52® or a vegetable oil such as vitamin E acetate, and saponins.

The vaccine according to the invention comprises an effective dosage of the NDV NP mutant as the active component, i.e. an amount of immunising NDV material that will induce immunity in the vaccinated birds against challenge by a virulent virus. Immunity is defined herein as the induction of a significant higher level of protection in a population of birds against mortality and clinical symptoms after vaccination compared to an unvaccinated group. In particular, the vaccine according to the invention prevents a large proportion of vaccinated animals against the occurrence of clinical symptoms of the disease and mortality.

Typically, the live vaccine can be administered in a dose of $10^{2.0}$–$10^{8.0}$ embryo infectious dose ($EID_{50}$), preferably in a dose ranging from $10^{4.0}$–$10^{7.0}$ $EID_{50}$. Inactivated vaccines may contain the antigenic equivalent of $10^{4.0}$–$10^{9.0}$ $EID_{50}$.

Inactivated vaccines are usually administered parenterally, e.g. intramuscularly or subcutaneously.

Although, the NDV vaccine according to the present invention may be used effectively in chickens, also other poultry such as turkeys, pigeons, quail, pheasants, guinea fowl and partridges may be successfully vaccinated with the vaccine. Chickens include broilers, reproduction stock and laying stock.

The age of the animals after post-hatch receiving a live or inactivated vaccine according to the invention is the same as that of the animals receiving the conventional live- or inactivated NDV vaccines. For example, broilers may be vaccinated at one-day old or at 1–3 weeks of age, particularly broilers with high levels of MDA. Laying stock or reproduction stock may be vaccinated at 1–10 days of age and boosted with a live or inactivated vaccine at 6–12 and 16–20 weeks of age.

The invention also includes combination vaccines comprising, in addition to the NDV NP mutant according to the invention, a vaccine strain capable of inducing protection against ND or against another avian pathogen.

Preferably, the combination vaccine additionally comprises one or more vaccine strains of Mareks Disease virus (MDV), infectious bronchitis virus (IBV), Newcastle disease virus (NDV), egg drop syndrome (EDS) virus, turkey rhinotracheitis virus (TRTV) or reovirus.

The additional ND vaccine strain in the combination vaccine, preferably, is a recombinant (virus) vaccine vector capable of expressing the F or HN protein of NDV. Such viral vaccine vectors are well known and their safety and efficacy have been extensively studied: Morgan et al., Avian Diseases 36, 858–870, 1992 and Avian Diseases 37, 1032–1040, 1993; Heckert et al., Avian Diseases 40, 770–777, 1996; Sakaguchi et al., Vaccine 16, 472–479, 1998 and Sonoda et al., J. Virol. 74, 3217–3226, 2000.

In a most preferred embodiment, the recombinant vaccine vector in a combination vaccine according to the invention is a recombinant HVT vector capable of expressing the NDV F or HN protein.

In case the combination vaccine is administered via the in ovo route the additional vaccine strain should be an embryo-safe vaccine strain, i.e. a live vaccine strain which, if inoculated into SPF eggs at embryonation day of 18, results in the hatching of at least 70% of the embryonated eggs.

The NDV marker vaccine described above, in conjunction with a diagnostic method, enables the distinction between animals that are vaccinated with it and animals that are infected with naturally occurring NDV strains or vaccinated with conventional ND vaccines.

The present invention also provides an invaluable tool to monitor ND control measures that may lead to eradication of NDV if applied in large scale stamping out programs. This tool concerns a method for determining NDV infection in a poultry comprising the step of examining a sample of the animal for the presence or absence of antibodies reactive with an immunodominant epitope located within a region of the NP having the amino acid sequence (447–455).

The sample of the animal used in this method may be any sample in which NDV antibodies can be detected, e.g. a blood, serum or tissue sample, a serum sample being preferred.

As an antigen in such a method use is made of a fragment of the NP comprising the (447–455) region as the sole epitope containing region. Therefore, a preferred method for determining NDV infection in an animal comprises the steps of:
(i) incubating a sample suspected of containing anti-NDV antibodies, with a fragment of the NP comprising the amino acid region (447–455) as the sole epitope containing region,
(ii) allowing the formation of antibody-antigen complex, and
(ii) detecting the presence of the antibody-antigen complex.

In a particular preferred diagnostic method the fragment of the NP is the polypeptide having the amino acid sequence 360–470 or a part thereof comprising the region (447–455).

In a most preferred diagnostic method the antigen used is the 18-mer peptide having the amino acid sequence 443–460.

The design of the immunoassay may vary. For example, the immunoassay may be based upon competition or direct reaction. Furthermore, protocols may use solid supports or may use cellular material. The detection of the antibody-antigen complex may involve the use of labelled antibodies; the labels may be, for example, enzymes, fluorescent-, chemiluminescent-, radio-active- or dye molecules.

Suitable methods for the detection of the NDV antibodies in the sample include the enzyme-linked immunosorbent assay (ELISA), immunofluorescent test (IFT) and Western blot analysis, the ELISA being preferred.

In an exemplifying ELISA, the wells of a polystyrene micro-titration plate are coated with an appropriate fragment of the NP comprising an immunodominant epitope. Next, the wells of the coated plates are filled with chicken serum and serial dilutions are made. After incubation, the presence or absence of the relevant chicken anti-NP serum antibodies directed against an immunodominant epitope is determined by a labelled (e.g. horse radish peroxidase conjugated) detecting antibody that binds to the captured anti-NP antibodies (if present in the test serum). The quantity of relevant antibodies present in the serum that bound to the NP fragment may be determined by incubating the plates with enzyme substrate and reading the absorbance value (OD) in a microplate autoreader.

In an alternative embodiment of the diagnostic method the presence of specific antibodies chicken serum is examined by incubating the serum and an appropriate antigen in the presence of a monoclonal antibody that specifically reacts with an epitope located within the (447–455) region.

Antibody detection-based ELISA's for NDV-infected versus NDV (subunit) vaccinated chickens, based on whole NP as the antigen have been described by Makkay et al., (1999, supra) and Errington et al. (J. Virol. Methods 55, 357–365, 1995) and the principle described herein may be applied accordingly when using the relevant antigen.

In a further embodiment of the present invention a diagnostic test kit is provided which is suitable for performing the diagnostic method according to the invention as described above.

In particular, a diagnostic test kit is provided which comprises in addition to the components usually present, an appropriate NP fragment as defined above, preferably the 18-mer (443–460) peptide, preferably coupled to a carrier molecule (if desired coated onto a solid phase), as the antigen reagent. Other components usually present in such a test kit include, biotin or horseradish peroxidase conjugated antibodies, enzyme substrate, washing buffer etc.

EXAMPLES

Example 1

Generation of a Recombinant NDV Lacking an Immunodominant Epitope on the Nucleoprotein (NP)

Materials and Methods

Introduction of Mutation into the Full-length NDV cDNA

In order to generate mutant NDVs, the plasmid pflNDV, expressing the full-length antigenome RNA of the lentogenic ND vaccine strain, Clone-30 (Römer-Oberdörfer et al., J. Gen. Virol. 80, 2987–2995, 1999), was used to introduce mutations. Internal deletions in the region where the immunodominant epitope is located were introduced using the "quick change site directed mutagenesis kit" according to the supplier's instructions (Stratagene). First, a DNA fragment encompassing nucleotides 77–2289 of NDV genome was prepared by digesting pflNDV with Mlul, filling with Klenow and treating with Apal. The ~2.2 kb DNA fragment was ligated into pSKT7T vector digested with Apal and EcoRI. PCR mutagenesis was then performed on the above described template using the following sets of primers (SEQ ID No: 5–10):

To delete nucleotides 1451–1486, corresponding to NP amino acids 444–455 P1A (5'-CCAGAAGCCGGG-GATGGG/AATAGCATGAGGGAG-3') SEQ ID NO. 5 P1B (5'-CTCCCTCATGCTATT/CCCATCCCCGGCTTCTGG-3') SEQ ID NO. 6

To delete nucleotides 1448–150, corresponding to NP amino acids 443–460 P2A (5'-CCAGAAGCCGGGGAT/GCGCCAAACTCTGCACAGG-3') SEQ ID NO.7 P2B(5'-CCTGTGCAGAGTTTGGCGC/ATCCCCGGCTTCTGG-3') SEQ ID NO.8

To delete nucleotides 1445–1588, corresponding to NP amino acids 442–489 P3A(5'-GGCAACCAGAAGC-CGGG/TGATGGAAAACCCAGC-3') SEQ ID NO. 9 P3B (5'-GCTGGGTTTTGTCCATCA/CCCGGCTTCTGGT-TGCC-3') SEQ ID NO. 10

Mutagenised clones were digested by Aatll/Apal and cloned into the same sites of pfJNDV.

Mutagenised clones were digested by Aatll/Apal and cloned into the same sites of pflNDV. The presence of the introduced mutations was confirmed by sequencing the respective clones. The resultant full-length clones, with deletions on the NP gene corresponding to amino acid positions 444–455, 443–460, or 442–489 were named NDV-Δ12, NDV-Δ18, and NDV-Δ48, respectively (FIG. 1).

Recovery of Recombinant Viruses

Approximately $1.5 \times 10^6$ BSR-T7/5 cells stably expressing phage T7 RNA polymerase were grown overnight to 90% confluency in 3.2 cm diameter culture dishes. Cells were transfected with plasmid mixtures containing 5 µg of pCite-NP, 2.5 µg of pCite-P, 2.5 µg of pCite-L and 10 µg of one of the full-length clones using a mammalian transfection kit (CaPO$_4$ transfection protocol; Stratagene). Three to five days after transfection, supernatants were harvested and inoculated into the allantoic cavity of 9- to 11-day old embryonated SPF chicken eggs. After 3–4 days of incubation, the presence of virus in the allantoic fluid was determined by rapid plate hemagglutination (HA) test using chicken erythrocytes.

Results

In order to delete the immunodominant epitope on the NP gene, or block expression of the C-terminal part of NP, the modifications described under materials and methods were carried out. Each modified full-length cDNA clone, together with three support plasmids expressing NDV NP, P, and L proteins, was transfected into BSR-T7/5 cells. After 3–5 days of incubation, supernatants were harvested and inoculated into 9- to 11-day old embryonated SPF chicken eggs. After 3–4 days of incubation, allantoic fluid samples were harvested and subjected to a HA test. HA was detected in eggs inoculated with the supernatant from cells transfected with the unmodified pflNDV. Surprisingly, NDV-Δ18 was detected using the HA test after one extra egg passage. NDV-Δ18 was then serially passaged for a total of eight passages in embryonated SPF eggs. RNA was isolated from cells infected with each passages and subjected to RT-PCR. In all the passages the introduced deletion was maintained, demonstrating the stability of the recombinant virus. Infectious virus was not detected in the allantoic fluid of embryonated eggs inoculated with supernatants obtained from NDV-Δ12 and NDV-Δ48 transfections, even after three successive egg passages.

Example 2

NDV-Δ18 can be used as a Marker Vaccine

Materials and Methods

Immunization of Chickens with NDV-Δ18 and Analysis of Sera

Fifteen SPF chickens at the age of 3 weeks were immunized with NDV-Δ18 by oculo-nasal route with a dose of 6.5 log$_{10}$ EID$_{50}$ per 0.2 ml and boosted 5 weeks after the first immunization with the same dose. Serum samples were collected just before vaccination and 2, 5, and 7 weeks after the first immunization. Serum samples were then tested by haemagglutination inhibition (HI) test and ELISAs to determine the level of seroconversion.

Enzyme Linked Immunosorbant Assay (ELISA)

An 18-mer synthetic peptide (SEQ ID No. 1) comprising the amino acid sequence (443–460) of the nucleoprotein was synthesized and coupled to bovine serum albumin (BSA). Briefly, the synthetic peptide (2 mg) was coupled to BSA (4:1 molar ratio, respectively) by using 20 mM glutaraldehyde in phosphate buffered saline (PBS) as a cross-linker. In parallel, a negative control antigen was prepared by cross-linking a BSA mixture without the addition of peptide. Following over night incubation at ambient temperature, cross-linking reaction was stopped by adding stabilizing buffer containing glycine to the reaction mixture. The BSA/peptide mixtures were aliquoted and stored at −20° C.

Microtiter plates were coated overnight at 2–8° C. with 0.5 µg synthetic peptide coupled to BSA or BSA alone in coating-buffer (carbonate-buffer, pH 9.6). Unbound antigen was removed by washing the wells four times with PBST-solution (PBS, Tween-20). Prior testing serum samples were diluted 50-fold in IB-EIA solution (0.2 M Na$_2$HPO4-2H$_2$O buffer, pH 7.0, 0.05% Tween-20, 0.5 M NaCl, 0.1% BSA) and added to the coated wells. Following 1.5 hour incubation at 37° C. in a humidified atmosphere, wells were washed with PBST-solution and incubated with 100 µl horseradish peroxidase conjugated rabbit anti-chicken immunoglobulins diluted in IB-EIA solution. After 45 minutes incubation at 37° C., wells were washed with PBST and the antigen-antibody complexes were detected by the addition of TMB as substrate. After 15 minutes incubation at ambient temperature the reaction was stopped by adding 50 µl 2 M sulphuric acid to each well. Optical densities were measured at 450 nm. Cut-off value (COV) was set three standard deviations above the average P/N ratios of negative control sample from SPF chickens (where P=the OD of samples from peptide coated wells and; N=the OD of samples from BSA coated wells).

In order to measure the entire NDV specific antibody response in serum panels tested, microtiter plates were coated with sucrose gradient purified NDV Clone 30 antigens. Briefly, wells were coated overnight with 0.5% Triton X-100 treated viral antigens (1.0 µg/ml) in 40 mM phosphate buffer (PBS, pH 7.2). Following removal of unbound antigens by washing with PBST, wells were post-coated with 10% v/v donor horse serum in PBS. Wells solely containing post-coated antigens were used as negative controls. Tested serum samples were diluted (1:150) in IB-EIA solution and added to both positive and negative control wells. The remaining incubation steps of the ELISA procedure were identical to the peptide-based ELISA as described above with the exception of the conjugate dilution buffer IB-EIA which was supplemented with 5% donor horse serum. Cut-off value (COV) was set three standard deviations above the average P/N ratios of negative control sample from SPF chickens.

Results

The sera from animals vaccinated with the recombinant NDV-Δ18 were collected 2, 5 and 7 weeks and subjected to HI test and ELISA. As shown in FIG. 2 the mean HI titers were 4.7, 4.9 and 7.7 at 2, 5, and 7 weeks after the first immunization, respectively. There was also a corresponding high reaction in the whole virus based ELISA, showing induction of a considerable immune response against the recombinant virus. In contrast, none of the sera reacted in the ELISA coated with the peptide, showing that chickens immunized with NDV-Δ18 completely lack antibodies directed against the immunodominant epitope on the NP protein, even after a booster immunization (sera at 7 weeks). Analysis of sera obtained from animals vaccinated with conventional inactivated or live virus vaccines showed reactivity against whole virus ELISA. Moreover, all tested sera were positive in the peptide based ELISA (FIG. 2), demonstrating the presence of antibodies directed against the immunodominant epitope of NP in the sera collected from animals immunized with conventional ND vaccines. Therefore, this peptide-based ELISA can discriminate the antibody response to the recombinant NDV-Δ18 from that of conventional ND strains.

Example 3

NDV-Δ18 as in ovo -Marker Vaccine Administered Alone or in Combination with Another Vector Vaccine Materials and Methods Virus Propagation in Embryonated Eggs To determine virus titer and embryo mortality, serial 10-fold dilutions of the recombinant NDV-Δ18 virus were prepared, and 9- to 11-day old embryonated SPF chicken eggs were inoculated into the allantoic cavity. The eggs were observed daily for embryo mortality for at least 7 days, and the 50% embryo-lethal dose ($ELD_{50}$) was determined using the method of Reed and Muench (Am. J. Hyg. 27, 493–497, 1938). A rapid plate HA test was also carried out on another set of eggs after 4 days of incubation, and the titer, expressed as 50% embryo-infectious dose ($EID_{50}$), was calculated using the same method.

In ovo Vaccination and Challenge

Eighteen-day old embryonated SPF chicken eggs were inoculated with the recombinant NDV-Δ18 virus alone or in combination with a HVT vector expressing NDV F protein (Morgan et al., Avian Dis. 37, 1032–1040, 1993). Using a 23 G needle, 0.1 ml of the virus dilution or negative allantoic fluid was injected, through a hole punched at the blunt end of the egg, just below the air sac membrane. Eggs were further incubated until hatch. The percent hatchability was recorded, and chickens were observed daily for general health. At 3 weeks of age, blood samples were taken and the sera were assayed for NDV antibodies in the NDV hemagglutination inhibition (HI) test and ELISAs. At 3 weeks of age, all animals were challenged with intramuscularly administered virulent NDV Herts strain. Chickens were observed daily for a period of 10 days for the occurrence of clinical signs of disease or mortality.

Results

NDV-Δ18 is Attenuated in Pathogenicity for Chicken Embryos

To determine the embryo-mortality caused by NDV-Δ18, 10-fold serial dilutions of passage 3 of NDV-Δ18 were inoculated into 11-day old embryonated SPF chicken eggs (0.2 ml/egg) and incubated for one week. Surprisingly, no specific embryo mortality was detected during the 7 days incubation period, showing that NDV-Δ18 was considerably attenuated for embryos (FIG. 3). Chicken embryos inoculated with the parent virus, recombinant NDV (rNDV), already started to die at three days post-inoculation, at doses higher than 4 $\log_{10}$ $EID_{50}$/ml. The difference between the 50% infectious dose and 50% lethal dose of rNDV was only 0.3 $\log_{10}$. In contrast, this difference was as high as 8.0 $\log_{10}$ for NDV-Δ18, showing that it was significantly attenuated (FIG. 3).

NDV-Δ18 is an Efficacious in ovo/Marker Vaccine

NDV-Δ18 was highly attenuated for chicken embryos when applied to 9- to 11-day old embryos, therefore an in ovo (embryo) vaccination experiment was carried out to determine the safety and efficacy of NDV-Δ18 (Table 1). Chickens hatched from in ovo vaccinated embryonated eggs were challenged with a velogenic Herts strain of NDV. Chickens vaccinated as embryos with NDV-Δ18 developed high antibody levels and the protection against lethal challenge was 100%, whether NDV-Δ18 is given alone or in combination with HVT recombinant expressing NDV-F (Table 1). All control chickens died within 3 days of challenge. These data show that NDV-Δ18 can confer full protection when administered to 18-day old SPF chicken embryos.

To determine whether animals vaccinated in ovo with NDV-Δ18 could be serologically distinguished from infected animals or from animals vaccinated with conventional vaccines, blood samples were collected at three weeks of age and subjected to ELISA as described in Example 2. As expected, all sera from NDV-Δ18 vaccinated animals did not react with the ELISA based on the peptide encompassing the immunodominant epitope on the NP gene, whereas all the sera were reactive with whole virus ELISA and in HI test (FIG. 4). This shows that in ovo administration of NDV-Δ18 did not affect the possibility to discriminate NDV-Δ18 vaccinated animals from that of infected animals. The absence of response to the immunodominant epitope on the NP gene was also confirmed when NDV-Δ18 was administered in ovo in combination with HVT-NDV/F, a vector vaccine expressing NDV fusion (F) protein (FIG. 4). This shows that NDV-Δ18 can be combined with other vector vaccines that do not express the immunodominant region of NDV nucleoprotein.

TABLE 1

Safety and efficacy of NDV-Δ18 or NDV-Δ18 plus HVT-NDV/F in SPF chickens vaccinated in ovo at 18 days of embryonation.

| Virus | Embryos | Dose [a] | Hatchability amount/total | HI titer [b] | Survival after challenge [c] |
|---|---|---|---|---|---|
| NDV-Δ18 | SPF | 3.2 | 25/30 (83%) | 5.1 ± 1.2 | 20/20 (100%) |
| NDV-Δ18 + | SPF | 4.2 | 18/27 (67%) | 4.6 ± 0.7 | 18/18 (100%) |

TABLE 1-continued Safety and efficacy of NDV-Δ18 or NDV-Δ18 plus HVT-NDV/F in SPF chickens vaccinated in ovo at 18 days of embryonation.

| Virus | Embryos | Dose [a] | Hatchability amount/total | HI titer [b] | Survival after challenge [c] |
|---|---|---|---|---|---|
| HVT-NDV/F | | 2.8 | | | |
| Control | SPF | — | 26/27 (96%) | 0.0 ± 0.0 | 0/20 (0%) |

[a] Dose in $\log_{10}$ EID$_{50}$ per egg for NDV and pfu per egg for HVT-NDV/F calculated after back titration of the samples
[b] Hemagglutination-inhibition (HI) titer (2log) against NDV at two weeks of age
[c] Chickens were challenged with Herts strain of NDV at three weeks of age with a dose of 5.5 $\log_{10}$ ELD$_{50}$/chicken intramuscularly.

As it is shown in Table 1, the hatchability of SPF animals was reduced, particularly when higher doses of NDV-Δ18 was used. To determine whether the presence of maternally derived antibodies (MDA) modulate the safety of NDV-Δ18, commercial chickens were vaccinated in ovo with NDV-Δ18 alone or in combination with HVT-NDV/F. Hatchability of embryonated commercial chicken eggs was completely unaffected by in ovo administration of NDV-Δ18 alone or in combination with HVT-NDV/F (Table 2), demonstrating the safety of NDV-Δ18 in animals with MDA.

TABLE 2

Safety of NDV-Δ18 or NDV-Δ18 in combination with HVT-NDV/F in commercial chickens vaccinated in ovo at 18 days of embryonation.

| Virus | Embryos | Dose [a] | Hatchability amount/total |
|---|---|---|---|
| NDV-Δ18 | Commercial | 4.2 | 29/30 (97%) |
| NDV-Δ18 +HVT-NDV/F | Commercial | 4.2<br>2.8 | 30/30 (100%) |
| Control [b] | Commercial | — | 27/30 (90%) |

[a] Dose in $\log_{10}$ EID$_{50}$ per egg for NDV and pfu per egg for HVT-NDV/F calculated after back titration of the samples.
[b] The mean HI titer of NDV specific MDA at the time of hatch was 5.3 ± 1.1.

In addition, hatchability was compared after administration of NDV-Δ18 at 18 or 19 days of embryonation. As it is shown in Table 3, hatchability of SPF embryos vaccinated at 19 days of embryonation was 100% compared to 76% for embryos vaccinated at 18 days of embryonation.

TABLE 3

Safety of NDV-Δ18 in SPF chickens vaccinated in ovo at 18 or 19 days of embryonation.

| Virus | Age of embryos | Dose $\log_{10}$ EID$_{50}$/egg | Hatchability amount/total |
|---|---|---|---|
| NDV-Δ18 | 18 days | 5.0 | 71% (15/21) |
| Control | 18 days | 0 | 100% (21/21) |
| NDV-Δ18 | 19 days | 5.0 | 100% 22/22) |
| Control | 19 days | 0 | 96% (21/22) |

Example 4

NDV-Δ18 as an Effective Post-hatch Marker Vaccine

Materials and Methods

To determine the safety and efficacy of NDV-Δ18 as a post-hatch vaccine, one-day-old SPF chickens were vaccinated by eye-drop route at a dose of 6 $\log_{10}$ EID$_{50}$/chick. Chickens were observed daily for clinical signs and at 3 weeks of age, blood samples were taken and all animals were challenged with intramuscularly administered virulent NDV Herts strain. Sera were assayed for NDV antibodies in the NDV hemagglutination inhibition (HI) test and ELISAs. Chickens were observed daily for a period of 2 weeks after challenge for the occurrence of clinical signs of disease or mortality.

Results

Chickens vaccinated after hatch with NDV-Δ18 developed NDV-specific antibodies and the protection against lethal challenge was greater than 90% at the administered dose (Table 4). All control chickens died within 3 days of challenge. During the observation period before challenge no vaccination related adverse signs were detected. To determine whether animals vaccinated with NDV-Δ18 could be serologically distinguished from infected animals or from animals vaccinated with conventional vaccines, blood samples collected just before challenge were subjected to ELISA as described in Example 2. As expected, all sera were reactive with whole virus ELISA and in HI test, but not with the ELISA based on the peptide encompassing the immunodominant epitope on the NP gene. Taken together, these data demonstrate that NDV-Δ18 is suitable not only for in ovo administration, but also is a safe and efficacious post-hatch marker vaccine.

TABLE 4

Safety and efficacy of NDV-Δ18 in one-day-old SPF chickens vaccinated by eye-drop route.

| Virus | Dose [a] | HI titer [b] | Survival after challenge [c] |
|---|---|---|---|
| NDV-Δ18 | 6.0 | 3.73 | 11/12 (92%) |
| Control | — | 0.0 | 0/5 (0%) |

[a] Dose in $\log_{10}$ EID$_{50}$ per chicken
[b] Hemagglutination-inhibition (HI) titer (2log) against NDV at 3 weeks of age
[c] Chickens were challenged with Herts strain of NDV at three weeks of age with a dose of 6.0 $\log_{10}$ ELD$_{50}$/chicken intramuscularly.

Example 5

A Marker Vaccine Expressing a Foreign Epitope

Materials and Methods

Construction and Generation of Recombinant Viruses

In order to determine the possibility of expressing a foreign epitope by a recombinant NDV, a well-characterised B-cell epitope of the S2 glycoprotein of murine hepatitis virus (MHV) (Talbot et al., Virology, 132, 250–260, 1984; Luytjes et al., J. Virol. 63, 1408–1415, 1989) was chosen to replace the NP-immunodominant epitope of NDV. The in-frame replacement substituted either 16 amino acids (nucleotide positions 1451 to 1499, corresponding to amino acids 444 to 459 of the NP) or 12 amino acid (nucleotide positions 1451 to 1486, corresponding to amino acids 444 to 455 of the NP) with two overlapping sequences of 16 amino acids (MHV epitope-1) or 10 amino acids (MHV epitope-2), respectively, encompassing the epitope on S2 glycoprotein of MHV.

Sequence of MHV epitope-1 (accession no. NCBI NC_001846; nucleotides 26464–26511 of whole genome; amino acids 845–860 of S2 protein):

```
5'-AGT CCT CTA CTT GGA TGC ATA GGT TCA ACA TGT GCT GAA GAC GGC AAT-3'
   Ser Pro Leu Leu Gly Cys Ile Gly Ser Thr Cys Ala Glu Asp Gly Asn
```

Sequence of MHV epitope-2 (accession no. NCBI NC_001846; nucleotides 26470–26499 of whole genome; amino acids 847–856 of S2 protein):

```
5'-CTA CTT GGA TGC ATA GGT TCA ACA TGT GCT-3'
   Leu Leu Gly Cys Ile Gly Ser Thr Cys Ala
```

PCR mutagenesis was performed on the 2.2 kb MluI/ApaI subclone described under Example 1 using appropriate pairs of primers:

Mutagenised clones were digested by AatII/ApaI and cloned into the same sites of pfINDV. The presence of the introduced mutations was confirmed by sequencing the respective clones. The resultant full-length clones, in which NP-amino acids 444–459 were replaced with MHV-epitope-1 sequence or NP-amino acids 444–455 were replaced with MHV-epitope-2 sequence, were named NDV-MHV1 and NDV-MHV2, respectively. Transfection and recovery of viruses was carried out as described in example 1. Three to five days after transfection, supernatants were harvested and inoculated into the allantoic cavity of 9- to 11-day old embryonated SPF chicken eggs. After 3–4 days of incubation, the presence of virus in the allantoic fluid was determined by rapid plate hemagglutination (HA) test using chicken erythrocytes.

Immunofluorescence Analysis

In order to determine the expression of the introduced MHV epitope, BSR-T7 cells were infected at a multiplicity of infection (moi) of 0.01 with the parent recombinant Clone-30, NDV-Δ18, NDV-MHV1 and NDV-MHV2. After 24 hr of incubation, infected cells were fixed with cold ethanol (96%) for 1 hr at room temperature. After washing three times with PBS, cells were incubated with monoclonal antibodies directed against the F protein, the immunodominant epitope of the NP protein or the MHV epitope. Cells were washed and stained with FITC conjugated anti-mouse antibody and examined by fluorescence microscopy.

Immunization of Chickens with NDV-MHV1 or NDV-MHV2 and Analysis of Sera

Two groups of each ten SPF chickens at the age of 3 weeks were immunized either with NDV-MHV1 or NDV-MHV2 by oculo-nasal route with a dose of 6.0 $\log_{10}$ $EID_{50}$ per 0.2 ml and boosted 5 weeks after the first immunization with the same dose. Serum samples were collected just before vaccination and 2, 5, and 7 weeks after the first immunization. Serum samples were tested by haemagglutination inhibition (HI) test and ELISAs to determine the level of seroconversion.

Enzyme Linked Immunosorbant Assay (ELISA)

To determine whether chickens immunized with NDV-MHV1 and NDV-MHV2 viruses had developed antibodies specific against the expressed MHV epitope, ELISA plates were coated with sucrose gradient purified MHV strain A59 antigen. Wells were coated overnight with 1% Triton X-100 treated viral antigen in 40 mM phosphate buffer (PBS, pH 7.2). Removal of unbound antigens, blocking and the remaining incubation steps of the ELISA procedure were identical to the whole-NDV-based ELISA as described under example 2. In order to determine the absence of response against the NP epitope, ELISA using the 18mer synthetic peptide encompassing the NP-immunodominant epitope was carried out as described under example 2. Similarly, the entire NDV specific antibody response was measured in ELISA plates coated with sucrose gradient purified NDV Clone 30 antigens as described under example 2.

Immunization and Challenge of Mice

To determine the protective ability of the MHV epitope expressed by NDV, groups of 4-weeks-old Balb/c female MHV-seronegative mice were used for immunization and challenge experiments. Two groups of each 10 mice were immunised with NDV-MHV1 or NDV-MHV2 at a dose of 6.0 $\log_{10}$ $EID_{50}$/mice and boosted with a similar dose 4 weeks later. Immunized as well as 10 control animals of similar age were challenged at 10 weeks of age (two weeks after the booster immunization) with wild type MHV A59 strain at adose of 10 $LD_{50}$/mice by intraperitoneal route. Animals were observed for clinical signs and mortality due to MHV for two weeks after challenge.

Results

Supernatants from transfected cells were harvested and passaged twice into 9- to 11-day-old embryonated SPF chicken eggs. Allantoic fluid samples were then harvested and subjected to HA test. HA was detected in eggs inoculated with the supernatant from cells transfected with NDV-MHV1 as well as NDV-MHV2 recombinants. The recovered viruses were further passaged two more times in embryonated eggs. The recovery of these recombinant viruses demonstrates that the NP-immunodominant epitope is not only dispensable for virus replication, but can also be replaced by entirely foreign sequence or epitope.

To determine whether the recombinant viruses express the newly introduced epitope, BSR cells were infected as described under materials and methods and subjected to immunofluorescence analysis. Using a monoclonal antibody (Mab) directed against the Fusion protein, the expression of F protein was indistinguishable in all viruses. In contrast, a Mab directed against the NP-immunodominant epitope reacted only with the parent virus Clone-30. As expected, a Mab directed against the MHV epitope reacted only with cells infected with NDV-MHV1 or NDV-MHV2, demonstrating that the epitope is properly expressed within the open-reading-frame of the NP gene.

Sera collected just before immunisation (T=0) and 7 weeks (T=7) after the first immunisation were then subjected to HI test and whole NDV ELISA. As shown in the figures, the HI titers in all chickens at 7 weeks after vaccination were above 6 $\log_2$ HI units and the reaction measured in the whole NDV based ELISA was also considerably high (FIGS. 5–8). Interestingly, 80% to 90% of chickens immunised with NDV-MHV1 or NDV-MHV2 reacted positively in an ELISA based on MHV whole virus antigen, demonstrating that chickens produce specific antibodies against the MHV epitope expressed by recombinant NDVs (FIGS. 9–11). In contrast, none of the sera reacted in the ELISA coated with the 18mer peptide, showing that chickens immunized with NDV-MHV1 or NDV-MHV2 completely lack antibodies directed against the immunodominant epitope on the NP. This property provides an extra security in the diagnostic test both, as a positive and negative marker and makes the recombinant viruses attractive dual marker candidates.

To further demonstrate the ability of the introduced epitope to protect against a lethal challenge, we immunized mice with the recombinant viruses and challenged them 6 weeks after the first immunization. Although mice are not natural hosts for NDV, significant level of protection was achieved in immunised mice against a lethal MHV challenge (Table 5). Therefore, these recombinant viruses are not only attractive as marker vaccines, but also as vectors to express foreign epitopes to protect against unrelated pathogen.

TABLE 5

| Virus | % survival after challenge |
| --- | --- |
| NDV-MHV1 | 70% (7/10) |
| NDV-MHV2 | 60% (6/10) |
| Control | 20% (2/10) |

FIGURE LEGENDS

FIG. 1. Recombinant NDV constructs. A schematic representation of the NDV gene order is shown in the negative-strand genomic RNA. Sequences around the immunodominant epitope on the NP gene (position 1442–1501, NP amino acids 441–460) are presented in a positive sense. Broken lines show deletions of 12 or 18 amino acids in NDV-Δ12 and NDV-Δ18, respectively. NDV-Δ48 possesses a C-terminal truncated NP (48 residues) as indicated by a sign of a stop codon (*) following the last amino acid.

FIG. 2. Fifteen SPF chickens were vaccinated by oculo-nasal route with NDV-Δ18 at three weeks of age and boosted once at 5 weeks of age. Sera samples collected just before vaccination (D18 0W), 2 weeks (D18 2W), 5 weeks (D18 5W) and 7 weeks (D18 7W) after the first vaccination were subjected to ELISA and HI test as described in materials and methods section. Serological response against a live commercial ND vaccine, Clone-30, was assessed in a similar manner from 19 SPF chickens vaccinated at one week of age and bled 4 weeks later. For the NEWCAVAC group, an inactivated commercial vaccine, 21 SPF chickens were vaccinated at 3 weeks of age and similar serological assays were performed in sera samples collected at 3 weeks after immunization. (D18=NDV-Δ18).

FIG. 3. Pathogenicity of rNDV and NDV-Δ18 in SPF chicken embryos. Eleven-day old embryonated SPF chicken eggs were inoculated with the parent rNDV or the mutant NDV-Δ18 and incubated for 7 days or until the death of embryos had occurred. NDV-Δ18 caused no embryo mortality for 7 days at all indicated dose, whereas rNDV was lethal even with a dose as low as 1 EID50/ml (approximately 10% mortality). Embryos inoculated with rNDV started to die as early as three days post-inoculation at higher doses.

FIG. 4. Serological response of SPF chickens vaccinated in ovo with NDV-Δ18 alone or in combination with HVT-NDV/F, a vector vaccine expressing NDV fusion protein. Animals were vaccinated at 18 days of embryonation and an HI test and ELISA were performed as described in materials and methods section with sera collected at three weeks of age. (D18=NDV-Δ18).

FIGS. 5–8. Serological response of SPF chickens vaccinated with NDV-MHV1 or NDV-MHV2. Serum samples collected just before vaccination (T=0) and 7 weeks (T=7) after the first vaccination were subjected to HI test and ELISA based on whole NDV antigen.

FIGS. 9–11. Chickens produce antibodies specific for MHV epitope. The same sera described under FIG. 5 (for NDV-MHV1 and NDV-MHV2) or FIG. 2 (for NDV-Δ18) were subjected to an ELISA based on whole MHV antigen

The invention claimed is:

1. A viable Newcastle disease virus (NDV) mutant lacking an immunodominant epitope found on an unmodified NDV protein as a result of a mutation in a gene encoding the protein, said epitope that is lacking being located within a region of the nucleoprotein (NP) of an unmodified NDV and having the amino acid sequence (447–455) shown in SEQ ID No. 1.

2. The NDV mutant according to claim 1, wherein the NDV mutant induces antiserum in poultry lacking antibodies that react with an immunodominant epitope located within the amino acid region (447–455) of the NP.

3. The NDV mutant according to claim 2, wherein the antiserum induced in poultry tacks antibodies that react with an 18-mer peptide having the NP amino acid sequence (443–460) shown in SEQ ID No. 2.

4. The NDV mutant according to claim 1, wherein the mutant comprises a deletion or substitution of one or more amino acids in a region of the NP protein having the amino acid sequence (447–455).

5. The NDV mutant according to claim 2, wherein the amino acids 443+/–1–460+/–1are deleted.

6. The NDV mutant according to claim 5, wherein the amino acids 443–460 are deleted.

7. The NDV mutant according to claim 4, wherein nucleotides encoding one or more amino acids in the region are substituted by a heterologous nucleic acid sequence encoding an immunodominant epitope of a polypeptide.

8. The NDV mutant according to claim 1, wherein the NDV mutant comprises additional attenuating mutations.

9. The NDV mutant according to claim 1, wherein the NDV mutant additionally comprises a heterologous nucleic acid sequence encoding an antigen of another avian pathogen.

10. A vaccine against Newcastle disease in poultry, comprising an effective amount of the NDV mutant of claim 1 in a live or inactivated form, and a pharmaceutically acceptable carrier or diluent.

11. The vaccine according to claim 10, wherein the vaccine additionally comprises at least one additional vaccine strain capable of inducing protection against ND or against another avian pathogen.

12. The vaccine according to claim 11, wherein the additional vaccine strain is a recombinant vaccine vector capable of expressing the F or HN protein of NDV.

13. The vaccine according to claim 12, wherein the recombinant vaccine vector is HVT.

14. The vaccine according to claim 11, wherein the additional vaccine strain is an embryo-safe vaccine strain.

15. A method for the protection of poultry against Newcastle disease comprising administering a vaccine according to claim 10 to the poultry.

16. The method according to claim 15, wherein the vaccine is administered via the in ovo route to an embryo.

17. A method for detecting NDV infection in poultry comprising the steps of:
  (i) incubating a sample suspected of containing anti-NDV antibodies; with a fragment of the NP region of NDV comprising an amino acid sequence selected from the group consisting of sequence (447–455) and sequence (443–460) as shown in SEQ. ID No. 2 as the sole epitope,
  (ii) allowing the formation of antibody-antigen complexes, and
  (iii) detecting the presence of the antibody-antigen complexes.

18. The method according to claim 17, wherein the NP fragment is a 18-mer peptide having the amino acid sequence (443–460) as shown in SEQ ID NO. 2.

19. A diagnostic test kit suitable for carrying out a method according to claim 17, comprising a NP fragment comprising the amino acid sequence (447–455) as shown in SEQ ID NO. 1.

20. A method for distinguishing vaccinated poultry from non-vaccinated poultry, wherein vaccinated poultry have been vaccinated with a vaccine according to claim 10, comprising extracting serum from the poultry and determining the presence or absence of antibodies reactive with an amino acid sequence (447–455) as shown in SEQ ID NO. 1, wherein serum from vaccinated poultry will lack antibodies reactive with said amino acid sequence.

* * * * *

```
                          SEQUENCE LISTING

<160> NUMBER OF SEQ ID NOS: 10

<210> SEQ ID NO 1
<211> LENGTH: 9
<212> TYPE: PRT
<213> ORGANISM: Newcastle disease virus
<220> FEATURE:
<223> OTHER INFORMATION: 9-mer peptide/epitope

<400> SEQUENCE: 1

Phe Leu Asp Leu Met Arg Ala Val Ala
 1               5

<210> SEQ ID NO 2
<211> LENGTH: 18
<212> TYPE: PRT
<213> ORGANISM: Newcastle disease virus
<220> FEATURE:
<223> OTHER INFORMATION: 18-mer peptide

<400> SEQUENCE: 2

Gly Glu Thr Gln Phe Leu Asp Leu Met Arg Ala Val Ala Asn Ser Met
 1               5                  10                  15

Arg Glu

<210> SEQ ID NO 3
<211> LENGTH: 1801
```

-continued

```
<212> TYPE: DNA
<213> ORGANISM: Newcastle disease virus
<220> FEATURE:
<221> NAME/KEY: CDS
<222> LOCATION: (122)

-continued

| | | | | | | | | | | | | |
|---|---|---|---|---|---|---|---|---|---|---|---|---|
|Ser|Tyr|Ile|Arg|Asn|Thr|Gly|Leu|Thr|Ala|Phe|Phe|Leu|Thr|Leu|Lys|
| | | |260| | | |265| | | |270| |

```
tac gga atc aac acc aag aca tca gcc ctt gca ctt agt agc ctc tca    985
Tyr Gly Ile Asn Thr Lys Thr Ser Ala Leu Ala Leu Ser Ser Leu Ser
        275                 280                 285 ggc gac atc cag aag atg aag cag ctc atg cgt ttg tat cgg atg aaa   1033
Gly Asp Ile Gln Lys Met Lys Gln Leu Met Arg Leu Tyr Arg Met Lys
        290                 295                 300 gga gat aat gcg ccg tac atg aca tta ctt ggt gat agt gac cag atg   1081
Gly Asp Asn Ala Pro Tyr Met Thr Leu Leu Gly Asp Ser Asp Gln Met
305                 310                 315                 320 agc ttt gcg cct gcc gag tat gca caa ctt tac tcc ttt gcc atg ggt   1129
Ser Phe Ala Pro Ala Glu Tyr Ala Gln Leu Tyr Ser Phe Ala Met Gly
                325                 330                 335 atg gca tca gtc cta gat aaa ggt act ggg aaa tac caa ttt gcc agg   1177
Met Ala Ser Val Leu Asp Lys Gly Thr Gly Lys Tyr Gln Phe Ala Arg
        340                 345                 350 gac ttt atg agc aca tca ttc tgg aga ctt gga gta gag tac gct cag   1225
Asp Phe Met Ser Thr Ser Phe Trp Arg Leu Gly Val Glu Tyr Ala Gln
        355                 360                 365 gct cag gga agt agc att aac gag gat atg gct gcc gag cta aag cta   1273
Ala Gln Gly Ser Ser Ile Asn Glu Asp Met Ala Ala Glu Leu Lys Leu
370                 375                 380 acc cca gca gca agg agg ggc ctg gca gct gct gcc caa cgg gtc tcc   1321
Thr Pro Ala Ala Arg Arg Gly Leu Ala Ala Ala Ala Gln Arg Val Ser
385                 390                 395                 400 gag gag acc agc agc ata gac atg cct act caa caa gtc gga gtc ctc   1369
Glu Glu Thr Ser Ser Ile Asp Met Pro Thr Gln Gln Val Gly Val Leu
                405                 410                 415 act ggg ctt agc gag ggg ggg tcc caa gct cta caa ggc gga tcg aat   1417
Thr Gly Leu Ser Glu Gly Gly Ser Gln Ala Leu Gln Gly Gly Ser Asn
        420                 425                 430 aga tcg caa ggg caa cca gaa gcc ggg gat ggg gag acc caa ttc ctg   1465
Arg Ser Gln Gly Gln Pro Glu Ala Gly Asp Gly Glu Thr Gln Phe Leu
        435                 440                 445 gat ctg atg aga gcg gta gca aat agc atg agg gag gcg cca aac tct   1513
Asp Leu Met Arg Ala Val Ala Asn Ser Met Arg Glu Ala Pro Asn Ser
        450                 455                 460 gca cag ggc act ccc caa tcg ggg cct ccc cca act cct ggg cca tcc   1561
Ala Gln Gly Thr Pro Gln Ser Gly Pro Pro Pro Thr Pro Gly Pro Ser
465                 470                 475                 480 caa gat aac gac acc gac tgg ggg tat tgatggacaa aacccagcct          1608
Gln Asp Asn Asp Thr Asp Trp Gly Tyr
                485 gcttccacaa aaacatccca atgccctcac ccgtagtcga ccctcgatt tgcggctcta   1668 tatgaccaca ccctcaaaca aacatccccc tctttcctcc ctcccctgc tgtacaactc   1728 cgcacgccct agataccaca ggcacaatgc ggctcactaa caatcaaaac agagccgagg   1788 gaattagaaa aaa                                                     1801

<210> SEQ ID NO 4
<211> LENGTH: 489
<212> TYPE: PRT
<213> ORGANISM: Newcastle disease virus

<400> SEQUENCE: 4

Met Ser Ser Val Phe Asp Glu Tyr Glu Gln Leu Leu Ala Ala Gln Thr
 1               5                  10                  15

Arg Pro Asn Gly Ala His Gly Gly Gly Glu Lys Gly Ser Thr Leu Lys
```

-continued

```
            20                  25                  30
Val Asp Val Pro Val Phe Thr Leu Asn Ser Asp Asp Pro Glu Asp Arg
             35                  40                  45

Trp Ser Phe Val Val Phe Cys Leu Arg Ile Ala Val Ser Glu Asp Ala
             50                  55                  60

Asn Lys Pro Leu Arg Gln Gly Ala Leu Ile Ser Leu Leu Cys Ser His
 65                  70                  75                  80

Ser Gln Val Met Arg Asn His Val Ala Leu Ala Gly Lys Gln Asn Glu
                     85                  90                  95

Ala Thr Leu Ala Val Leu Glu Ile Asp Gly Phe Ala Asn Gly Thr Pro
                100                 105                 110

Gln Phe Asn Asn Arg Ser Gly Val Ser Glu Glu Arg Ala Gln Arg Phe
                115                 120                 125

Ala Met Ile Ala Gly Ser Leu Pro Arg Ala Cys Ser Asn Gly Thr Pro
                130                 135                 140

Phe Val Thr Ala Gly Ala Glu Asp Ala Pro Glu Asp Ile Thr Asp
145                 150                 155                 160

Thr Leu Glu Arg Ile Leu Ser Ile Gln Ala Gln Val Trp Val Thr Val
                165                 170                 175

Ala Lys Ala Met Thr Ala Tyr Glu Thr Ala Asp Glu Ser Glu Thr Arg
                180                 185                 190

Arg Ile Asn Lys Tyr Met Gln Gln Gly Arg Val Gln Lys Lys Tyr Ile
                195                 200                 205

Leu Tyr Pro Val Cys Arg Ser Thr Ile Gln Leu Thr Ile Arg Gln Ser
                210                 215                 220

Leu Ala Val Arg Ile Phe Leu Val Ser Glu Leu Lys Arg Gly Arg Asn
225                 230                 235                 240

Thr Ala Gly Gly Thr Ser Thr Tyr Tyr Asn Leu Val Gly Asp Val Asp
                    245                 250                 255

Ser Tyr Ile Arg Asn Thr Gly Leu Thr Ala Phe Phe Leu Thr Leu Lys
                260                 265                 270

Tyr Gly Ile Asn Thr Lys Thr Ser Ala Leu Ala Leu Ser Ser Leu Ser
                275                 280                 285

Gly Asp Ile Gln Lys Met Lys Gln Leu Met Arg Leu Tyr Arg Met Lys
                290                 295                 300

Gly Asp Asn Ala Pro Tyr Met Thr Leu Leu Gly Asp Ser Asp Gln Met
305                 310                 315                 320

Ser Phe Ala Pro Ala Glu Tyr Ala Gln Leu Tyr Ser Phe Ala Met Gly
                325                 330                 335

Met Ala Ser Val Leu Asp Lys Gly Thr Gly Lys Tyr Gln Phe Ala Arg
                340                 345                 350

Asp Phe Met Ser Thr Ser Phe Trp Arg Leu Gly Val Glu Tyr Ala Gln
                355                 360                 365

Ala Gln Gly Ser Ser Ile Asn Glu Asp Met Ala Ala Glu Leu Lys Leu
                370                 375                 380

Thr Pro Ala Ala Arg Arg Gly Leu Ala Ala Ala Gln Arg Val Ser
385                 390                 395                 400

Glu Glu Thr Ser Ser Ile Asp Met Pro Thr Gln Gln Val Gly Val Leu
                    405                 410                 415

Thr Gly Leu Ser Glu Gly Gly Ser Gln Ala Leu Gln Gly Gly Ser Asn
                420                 425                 430

Arg Ser Gln Gly Gln Pro Glu Ala Gly Asp Gly Glu Thr Gln Phe Leu
                435                 440                 445
```

-continued

Asp Leu Met Arg Ala Val Ala Asn Ser Met Arg Glu Ala Pro Asn Ser
    450                 455                 460

Ala Gln Gly Thr Pro Gln Ser Gly Pro Pro Pro Thr Pro Gly Pro Ser
465                 470                 475                 480

Gln Asp Asn Asp Thr Asp Trp Gly Tyr
                485

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: NP primer
      P1A

<400> SEQUENCE: 5
ccagaagccg gggatgggaa tagcatgagg gag                           33

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: NP primer
      P1B

<400> SEQUENCE: 6
ctccctcatg ctattcccat ccccggcttc tgg                           33

<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence: NP primer
      P2A

<400> SEQUENCE: 7
ccagaagccg gggatgcgcc aaactctgca cagg                          34

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence: NP primer
      P2B

<400> SEQUENCE: 8
cctgtgcaga gtttggcgca tccccggctt ctgg                          34

<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence: NP primer
      P3A

<400> SEQUENCE: 9
ggcaaccaga agccgggtga tggacaaaac ccagc                         35

<210> SEQ ID NO 10
<211> LENGTH: 35
<212> TYPE: DNA

```
<213> ORGANISM: Artificial Sequence
<220> FEATURE:
<223> OTHER INFORMATION: Description of Artificial Sequence: NP primer
      P3B

<400> SEQUENCE: 10
gctgggtttt gtccatcacc cggcttctgg ttgcc                              35
```